United States Patent [19]

Kita et al.

[11] 4,202,942

[45] May 13, 1980

[54] DESTRUCTION BY FERMENTATION OF 2-KETOGLUCONATE IN THE PRESENCE OF 2-KETOGULONATE

[75] Inventors: Donald A. Kita, Essex; John W. Gagne, Norwich; Dennis M. Fenton, Gales Ferry, all of Conn.

[73] Assignee: Pfizer Inc., New York, N.Y.

[21] Appl. No.: 926,262

[22] Filed: Jul. 20, 1978

[51] Int. Cl.² .............................................. C12B 1/00
[52] U.S. Cl. ................................................ 435/262
[58] Field of Search ............................ 195/2; 435/262

[56] References Cited

U.S. PATENT DOCUMENTS

| | | | |
|---|---|---|---|
| 2,301,811 | 11/1942 | Reichstein | 562/578 X |
| 2,987,448 | 6/1961 | Goering | 195/2 |
| 3,790,444 | 2/1974 | Oga et al. | 195/47 |

FOREIGN PATENT DOCUMENTS 59584 7/1947 Netherlands .
443901 4/1936 United Kingdom .

*Primary Examiner*—Raymond N. Jones
*Assistant Examiner*—Robert J. Warden

[57] ABSTRACT

2-Ketogluconate present in a mixture with 2-ketogulonate is destroyed by fermentation with a strain of a Pseudomonas species leaving desired 2-ketogulonate intact. Subsequent hydrolysis of the 2-ketogulonate yields ascorbic acid.

2 Claims, No Drawings

DESTRUCTION BY FERMENTATION OF 2-KETOGLUCONATE IN THE PRESENCE OF 2-KETOGULONATE

BACKGROUND OF THE INVENTION

2-Keto-L-Gulonic acid is an important intermediate in vitamin C manufacture. Condensation of L-sorbose with acetone in the presence of sulfuric acid followed by oxidation with permanganate and hydrolysis of the diisopropylidene derivative by boiling yields 2-keto-L-gulonic acid as described in Helv. Chim. Acta. 17, 311 (1934) and U.S. Pat. No. 2,301,811. The preparation of 2-keto-L-gulonic acid by careful oxidation of L-sorbose with nitric acid is claimed in British Pat. No. 443,901 and Dutch Pat. No. 59,584. The selective reduction of 2,5-diketogluconic acid to yield a mixture of 2-ketogluconic acid and 2-ketogulonic acid with subsequent hydrolysis of the 2-ketogulonic acid to afford ascorbic acid is described in co-pending application, Ser. No. 843,946, filed Oct. 20, 1977.

SUMMARY OF THE INVENTION

The present invention is concerned with a process for destroying 2-ketogluconate in a mixture containing 2-ketogulonate by fermentation with a selected strain of a Pseudomonas species thus facilitating the recovery and purification of the ascorbic acid produced by the subsequent hydrolysis of the remaining intact 2-ketogulonate.

DETAILED DESCRIPTION OF THE INVENTION 2,5-Diketogluconic acid is a useful intermediate in the synthesis of vitamin C. It is readily prepared by bacterial action on glucose such as the process described in U.S. Pat. No. 3,790,444. Selective reduction of the 2,5-diketogluconic acid in the fermentation broth by the process described in co-pending application, Ser. No. 843,946, filed Oct. 20, 1977, yields a 85:15 mixture of 2-ketogulonic acid and 2-ketogluconic acid. Subsequent hydrolysis affords a mixture of ascorbic and erythorbic acids.

It is desirable that the 2-ketogluconic acid present in the reduced fermentation broth described above be removed or substantially reduced in concentration leaving remaining 2-ketogulonate intact so that subsequent hydrolysis affords ascorbic acid only.

The present invention is concerned with a novel process for the fermentative destruction of 2-ketogluconic acid in the presence of 2-ketogulonic acid employing a selected strain of a Pseudomonas species.

A variety of microorganisms were tested for their ability to metabolize 2-ketogluconic acid to carbon dioxide and water without affecting co-existing 2-ketogulonic acid. Among the organisms screened, those belonging to the genus Pseudomonas were capable of selectively destroying 2-ketogluconic acid, and these were strains of Pseudomonas fluorescens. Workable cultures readily obtainable from publicly held depositories are Pseudomonas fluorescens NRRL B10 and Pseudomonas fluorescens ATCC 13430.

These cultures are readily propagated in aqueous nutrient media containing a source of assimilable carbon, assimilable nitrogen and inorganic salts. Organic nitrogen provided by peptone and meat extract is preferred for the first stage inoculum medium. Corn steep liquor, diammonium hydrogen phosphate and urea are the preferred nitrogen sources for the second stage inoculum and final fermentation media.

An aliquot of a 24 hour shake flask culture of a suitable strain of Pseudomonas fluorescens sufficient to provide a 5% inoculum is transferred to a nutrient medium contained in a fermentor held at a bath temperature of 28°–30° C. with mechanical stirring at about 1700 r.p.m. and an aeration rate of about 0.75 volume of air per volume of broth per minute. After a period of about 20 hours, an aliquot sufficient to provide a 5% inoculum is transferred to a fermentor containing a corn steep liquor, inorganic ammonium salts and urea nutrient medium. Increased growth may be obtained by the addition of 0.5 g/l of flucose. The propagation is conducted at a temperature of about 28°–30° C. with mechanical stirring at 1700 r.p.m. and aeration at 0.75 volume of air per volume of broth per minute. At a period of 8 hours a mixture of 2-ketogluconate and 2-ketogulonate obtained by the selective reduction of 2,5-diketogluconate (copending application Ser. No. 843,946, filed Oct. 20, 1977) is added and the fermentation continued until the destruction of the 2-ketogluconate is substantially complete as determined by high pressure liquid chromatography (approximately 24 hours). The destruction rate of 2-ketogluconate may be increased by the further addition of 5 g/l of corn steep liquor or 0.5–1.0 g/l of urea.

The added 2-ketogluconate - 2-ketogulonate mixture may be provided by the selective reduction of pure or crude 2,5-diketogluconate or preferably and advantageously by fermentation broth containing the mixture obtained by the selective reduction of the 2,5-diketogluconate produced by bacterial action on glucose.

Varying equivalents of an alkali metal borohydride per mole of 2,5-diketogluconate afford ratios of 2-ketogulonate:2-ketogluconate of 85:15 to 45:55 in the reduced fermentation broths.

Generally, fermentation broths containing higher ratios of 2-ketogulonate to 2-ketogluconate (85:15) are preferred for further processing, i.e., destruction of 2-ketogluconate by Pseudomonas fluorescens fermentation and subsequent hydrolysis of remaining intact 2-ketogulonic acid to yield ascorbic acid.

As used in the specification and claims hereof, the terms 2,5-diketogluconate, 2-ketogluconate and 2-ketogulonate include the free acids and salts thereof.

EXAMPLE 1

The following aqueous inoculum medium is prepared:

| Ingredient | Grams/liter |
| --- | --- |
| Glucose | 25 |
| Corn Steep liquor | 5 |
| $KH_2PO_4$ | 0.5 |
| $K_2HPO_4$ | 0.5 |
| $MgSO_4 . 7H_2O$ | 0.2 |
| $CaCO_3$ | 6.3 |
| pH-6.2 | |

A shake flask containing one liter of medium is autoclaved for 30 minutes at 121° C. The pH of the cooled medium is 6.0 Cells of Acetobacter cerinus IFO 3263 from a nutrient agar slant (5 ml of a 20 ml sterile aqueous suspension) are added to the flask which is then shaken on a rotary shaker at about 28° C. for about 24 hours.

An aliquot of the culture growth sufficient to provide a 5%, inoculum is added to a 4-liter stirred fermentor containing 2 liters of the following production medium:

| Ingredient | Grams/liter |
| --- | --- |
| Glucose | 110 |
| Corn steep liquor | 0.5 |
| (NH4)2HPO4 | 0.58 |
| KH2PO4 | 1.5 |
| MgSO4 . 7H2O | 0.5 |
| Urea | 0.5 |
| CuSO4 . 5H2O | 1 mg |
| Nicotinic acid | 300 micrograms |
| pH-6.0 | |

The fermentation is conducted at a temperature of about 28° C. with stirring at 1700 r.p.m. and aeration at the rate of 0.75 volume of air per volume of broth per minute. After a fermentation period of about 20 hours, sterile glucose is added (55 grams per liter). The pH is maintained by the addition of sodium hydroxide solution. The fermentation is continued until a yield of 2,5-diketogluconic acid of 95% (based on glucose) is obtained.

EXAMPLE 2

To a rapidly stirring solution of 20 liters of filtered crude fermentation broth containing 10% sodium 2,5-diketogluconate (0.84M) from Example 1 at 0° C. is added 42.4 ml of 2.2M NaBh4 in 7M HaOH (0.93M of hydrogen) at a rate of 1 ml/minute. The pH of the solution increases rapidly from 3.65 to 10.2. The resulting slurry is filtered, the filtrate adjusted to ph 1.6 with concentrated H2SO4 and the resulting precipitate is removed by filtration and discarded. The pH of the filtrate is adjusted to 7.0 with sodium hydroxide. 2-Ketogulonate - 2-ketogluconate ratio is 85:15.

EXAMPLE 3

The following aqueous inoculum medium is prepared:

| Ingredient | Grams/liter |
| --- | --- |
| Meat extract | 4 |
| Yeast extract | 4 |
| Peptone | 4 |
| Glucose | 10 |
| NaCl | 2 |
| pH-6.2 | |

A shake lask containing one liter of medium is autoclaved for 30 minutes at 121° C. Cells of Pseudomonas fluorescens NRRL BlO from a nutrient agar slant are added to the flask which is then shaken on a rotary shaker at about 28° C. for about 24 hours.

An aliquot of the culture growth sufficient to provide a 5% inoculum is added to a 4-liter stirred fermentor containing 2 liters of the following medium:

| Ingredient | Grams/liter |
| --- | --- |
| Corn steep liquor | 8 |
| (NH4)2HPO4 | 1 |
| KH2PO4 | 1 |
| MgSO4 . 7H2O | 0.5 |
| Glucose | 10 |
| Urea | 2 |
| pH-7.0 | |

The fermentation is conducted at a temperature of about 28°-30° C. with stirring at 1700 r.p.m. and aeration at the rate of 0.75 volume per volume of broth per minute. After a fermentation period of about 20 hours an aliquot sufficient to provide a 5% inoculum is transferred to a 4-liter fermentor containing 2 liters of the following culture medium:

| Ingredient | Grams/liter |
| --- | --- |
| Corn steep liquor | 10 |
| (NH4)2HPO4 | 2 |
| KH2PO4 | 1 |
| MgSO4 . 7H2O | 0.5 |
| Urea | 2 |
| pH - 7.0 | |

Propagation is conducted at a temperature of about 28°-30° C. with stirring at 1700 r.p.m. and aeration at the rate of 0.75 volume of air per volume of broth per minute. After a fermentation period of about 8 hours, an aliquot sufficient to provide a 10% inoculum is transferred to a fermentor containing the reduced fermentation broth of Example 2 at pH 7.0. The fermentation is continued at a temperature of 28°-30° C., stirring at 1700 r.p.m. and aeration at 0.75 volume of air per volume of broth per minute until the destruction of 2-ketogluconate is substantially complete.

The filtered fermentation broth may be processed by the addition of xylene and concentrated hydrochloric acid and heated at 65° C. for about 5 hours with stirring. Ascorbic acid is recovered from the reaction mixture and purified by crystallization.

EXAMPLE 4

Sodium 2,5-diketogluconate (15 grams) is dissolved in 150 ml of water and 6.61 grams of sodium carbonate is added with stirring at 0° C. The pH of the solution increases to 9.57. Sodium borohydride (0.49 grams) is added and the solution stirred at 0° C. for about 15 minutes to afford a mixture of 2-ketogulonate - 2-ketogluconate in the ratio of 85:15.

A culture broth containing growing cells of Pseudomonas fluorescens ATCC 13430 is added to the neutralized reduced solution above and the 2-ketogluconate destroyed by the process of Example 3.

What is claimed is:

1. A process for destroying 2-ketogluconate in a mixture containing 2-ketogulonate and said 2-ketogluconate which comprises contacting said mixture with a growing culture of Pseudomonas fluorescens strain ATCC 13430 in an aqueous nutrient medium and continuing the fermentation until said 2-ketogluconate is substantially destroyed.

2. The process of claim 1 wherein said 2-ketogluconate and 2-ketogulonate mixture is contained in selectively reduced fermentation broth obtained by the borohydride reduction of 2,5-diketo-gluconate produced by bacterial action on glucose.

UNITED STATES PATENT AND TRADEMARK OFFICE
CERTIFICATE OF CORRECTION

PATENT NO. : 4,202,942

DATED : May 13, 1980

INVENTOR(S) : Donald A. Kita et al

It is certified that error appears in the above-identified patent and that said Letters Patent are hereby corrected as shown below:

In the following places italicize "Pseudomonas":

| Abstract | lines 2-3 | Column 1 | line 27 |
| Column 1 | line 52 | Column 1 | line 57 |

In the following places italicize "Pseudomonas fluorescens":

| Column 1 | line 59 | Column 1 | line 60 |
| Column 1 | line 61 | Column 2 | line 4 |
| Column 2 | line 42 | Column 3 | lines 56-57 |

Column 2 line 14 change "flucose" to -- glucose --.

Column 2 line 64 italicize "Acetobacter cerinus".

UNITED STATES PATENT AND TRADEMARK OFFICE
CERTIFICATE OF CORRECTION

PATENT NO. : 4,202,942        Page 2 of 2
DATED : May 13, 1980
INVENTOR(S) : Donald A. Kita et al It is certified that error appears in the above-identified patent and that said Letters Patent are hereby corrected as shown below:

Column 3 line 33 change "NaBh" to -- $NaBH_4$ --.

Column 3 line 33 change "HaOH" to -- NaOH --.

Column 3 line 36 change "ph" to -- pH --.

Column 3 line 55 change "lask" to -- flask --.

Signed and Sealed this

Thirtieth Day of December 1980

[SEAL]

Attest:

SIDNEY A. DIAMOND

Attesting Officer      Commissioner of Patents and Trademark